United States Patent
Arcas et al.

(10) Patent No.: US 7,521,673 B2
(45) Date of Patent: Apr. 21, 2009

(54) WIDE RANGE, VERY HIGH RESOLUTION DIFFERENTIAL MOBILITY ANALYZER (DMA)

(75) Inventors: Emilio Ramiro Arcas, Madrid (ES); Angel Rivero Jimenez, Madrid (ES)

(73) Assignee: RAHEM, S.A., Madrid (ES)

( * ) Notice: Subject to any disclaimer, the term of this patent is extended or adjusted under 35 U.S.C. 154(b) by 366 days.

(21) Appl. No.: 11/508,217

(22) Filed: Aug. 23, 2006

(65) Prior Publication Data

US 2007/0044580 A1 Mar. 1, 2007

Related U.S. Application Data

(60) Provisional application No. 60/710,609, filed on Aug. 24, 2005.

(51) Int. Cl.
*G01N 15/00* (2006.01)

(52) U.S. Cl. .............. 250/294; 250/281; 250/287; 250/288; 73/28.04; 73/865; 73/865.5; 324/452

(58) Field of Classification Search .............. 250/281, 250/282, 286, 287, 288, 294; 73/28.04, 865, 73/865.5; 324/452
See application file for complete search history.

(56) References Cited

U.S. PATENT DOCUMENTS

| | | | |
|---|---|---|---|
| 5,936,242 A * | 8/1999 | De La Mora et al. | 250/288 |
| 6,567,157 B1 * | 5/2003 | Flagan et al. | 356/37 |
| 7,199,362 B2 * | 4/2007 | Rockwood et al. | 250/286 |
| 2002/0098653 A1 * | 7/2002 | Flagan et al. | 438/260 |
| 2005/0045818 A1 * | 3/2005 | De La Mora et al. | 250/294 |
| 2006/0289745 A1 * | 12/2006 | Miller et al. | 250/294 |
| 2007/0272847 A1 * | 11/2007 | Labowsky et al. | 250/283 |

\* cited by examiner

*Primary Examiner*—Jack I Berman
*Assistant Examiner*—Michael J Logie
(74) *Attorney, Agent, or Firm*—Birch, Stewart, Kolasch & Birch, LLP

(57) ABSTRACT

The resolution of a differential mobility analyzer (DMA) and the range of valid mobility values for the charged particles that it can detect are increased. The DMA makes use of a flat configuration and a purely two-dimensional operating model in which shims are used for improved adjustment and precision of the parallel faces that make up the analysis area. The analyzer uses a closed and pressurized aerodynamic tunnel to establish a cross flow with a very high Reynolds number.

27 Claims, 5 Drawing Sheets

# WIDE RANGE, VERY HIGH RESOLUTION DIFFERENTIAL MOBILITY ANALYZER (DMA)

This Nonprovisional application claims priority under 35 U.S.C. 119 (e) on U.S. Provisional Application No(s). 60/710,609 filed on Aug. 24, 2005 the entire contents of which are hereby incorporated by reference.

OBJECT OF THE INVENTION

This invention refers to a wide range, very high-resolution differential mobility analyzer (DMA), in which resolution is increased with regard to those known in the state of the art and in which the range of valid mobility values for the charged particles that it can simultaneously detect is also increased.

This invention is characterized by a flat configuration and a purely two-dimensional operating model in which shims are used for the improved adjustment and precision of the parallel faces forming the area of analysis and that directly affect the improvement of the resolution presented. Likewise, in the inlet face, a slot is used for injection, with the extraction of charged particles being carried out by means of a second slot.

This differential mobility analyzer is characterized by the use of one or more multi-track electric charge sensors. When an outlet slot or slit is used, the multi-track charge sensors are located above, below or simultaneously above and below the outlet slot, allowing quicker adjustment, as well as the simultaneous mobility readings, depending on the point of impact. Likewise, it includes the use of more than one outlet slot, together with its multi-track charge sensors.

Additionally, the differential mobility analyzer may have a non-linear module in its outlet that distinguishes between particles of very similar mobility in the linear range but whose behaviour is different in the non-linear range.

It is characterized by the use of flows with high Reynolds numbers situated between $10^5$ and $10^6$ and with a turbulence level of less than 0.1%, which is possible thanks to a careful design of all the parts involved in the flow, among which the presence of a closed and pressurized aerodynamic tunnel stands out.

BACKGROUND OF THE INVENTION

Differential mobility analyzer's (DMAs) are devices that are known for their use both in the laboratory and commercially. These devices seek to detect and analyse substances that are discriminated on the basis of the different ionic mobility of the charged particles.

A charged particle subjected to an electric field is accelerated in the direction of the field. If the ionized particle is immersed in a fluid, there is a resistance to the movement which prevents the particle from accelerating indefinitely, rather that it quickly attains a limit speed due to the balance between the electrical force that makes it accelerate and the resistance to movement caused by the fluid. This situation of balance establishes a value for the limit speed per unit of electric field [$m^2$/Vs], called the ionic mobility limit, which mainly depends on the specific size and configuration of the charged particle, on the dynamic viscosity of the fluid, as well as on the strength of the electric field.

On the basis of this phenomenon, differential mobility analyzers establish an electric field with two electrodes in an area normally known as the analysis area, crossed by a cross flow in stationary conditions.

A charged particle that is injected into an electrode tends to travel to the other electrode due to the action of the electric field; nevertheless, the presence of a cross flow drags the particle in such a way that it will not impact following the line of the electric field, but at a point downstream.

The point of impact is different depending on the type of particle, since the mobility is the property that allows the discrimination of the substance of interest.

The resolution of this type of device depends, as described in U.S. Pat. No. 6,787,763, on the degree with which the turbulence in the cross flow is minimized, as well as of the Brownian diffusion.

The presence of turbulence causes fluctuations with respect to the average field of speeds that disperse the charged particle's trajectory and, when the average free travel of the particle is high due to the presence of reduced pressures or high typical residence times, the effects of the Brownian movement are greater.

The dimensionless Reynolds and Peclet numbers, defined as:

$$Re = L \cdot v / \nu;$$

$$Pe = L \cdot v / D;$$

Where v is a typical speed, L a typical length, $\nu$ is the kinematic viscosity and D the molecular or Brownian coefficient of diffusion.

All these effects, turbulent diffusion and Brownian dispersion, are fully described and it has been proven that they depend on the Reynolds and Peclet numbers; and that these must be as high as possible in order to increase the resolution. Although it is known that, in general, for the flow in conduits, a Reynolds number of around 2000 is a critical value, above which the flow is turbulent, under certain conditions it is possible to maintain the laminar flow above this Reynolds value or with a small level of turbulence.

Mainly, the presence of favorable gradients of pressure that are sought for in all areas of the conduit, maintaining the boundary layer attached to the walls without its separation, preventing it from growing unnecessarily and eliminating the presence of disturbances (vibrations, roughness) that could release instabilities and increase the level of background turbulence.

The references cited in the background section of U.S. Pat. No. 6,787,763 are included for reference, noting that the said patent claims to reach Reynolds numbers in the range of $10^5$. The geometry that is used in this analyzer is cylindrical, where there are factors of imprecision which cannot be avoided:

The cylindrical geometry has a central rod with cylindrical symmetry on which coaxiality has to be ensured and, given that this rod consists of more than one piece, its thinness and the machining errors of each piece and of the seatings accumulate, prejudicing coaxiality. This type of configuration requires at least five adjustments to achieve coaxiality. The lack of coaxiality, however small it may be, has an important effect on the electric field, which is very sensitive to this factor.

The use of cylindrical geometries does not offer any absorption of coaxial vortices in the duct which could induce oscillations in the flow.

In this type of device, once knowing the degrees of expansion and contraction to be normally high, being important sources of turbulence.

In current devices, the perimeter feed is carried out non-uniformly, which means that the reading conditions do not match a correct condition of cylindrical symmetry.

The cross flow feeds in this type of device undergo sudden expansions that are not always stabilised down stream.

The long length of the inlet mouth of the analyzer and the use of very small accelerations are described as inconveniences in the section of this patent dedicated to the state of the art.

In U.S. Pat. No. 6,787,763, use is made of the cylindrical configuration in which the inconveniences of the flat analyzer described in U.S. Pat. No. 5,869,831 are said to have been overcome.

It must be said that, although a flat analyzer is used in U.S. Pat. No. 5,869,831, both the injection or insertion of charged particles and the extraction are carried out via holes. It is enough to consider that the presence of instabilities in the flow or in the electric field could cause a very large adjustment problem, since the trajectory does not avoid three-dimensional effects in the direction perpendicular to the plane defined by the electric field and in the main direction of the cross flow. These deviations must also be controlled so that the adjustment of these factors causes the treatment of this analyzer to be three-dimensional in practice and not two-dimensional even though planes are used.

Although there are classifiers with configurations that are very close to two-dimensional behaviours with laminar flow conditions in the field of aerosols, these are made for particles that are injected with a secondary flow that causes a mixing layer that induces turbulence and a three-dimensional aspect, as well as an important change in the original profile of the speeds of the cross flow. Likewise, this type of device works with pressures that are lower than atmospheric pressure and with speeds in the subsonic or incompressible range.

Publication number WO2004048924 describes a method and apparatus for carrying out an ionic mobility spectrometry Use is made of a cross flow with an electric field. An ionizer injects the ions into the working volume perpendicular to the direction of the electric field, contrary to normal practice in a DMA, in such a way that the particle undergoes a double drag: one drag in the direction of the flow and which is in the same direction as that of the entry of the ionized particles, and a perpendicular drag due to the electric field. The combination of the two forces causes a trajectory that is, in principle, curved which depends on the ion's electrical mobility to reach a point that is more or less further away.

The spectrum readings are carried out in a vectorial charge sensor that provides different values for the deposited charge according to the incidence point. Given that the measurements are made within a specific time period, it is necessary to reset the instrument to zero before carrying out each test.

In all the backgrounds considered, the DMAs analyzed place the emphasis on their internal configuration, but not on upstream and downstream flow conditions. This invention includes a closed-circuit, pressurized, aerodynamic wind tunnel that prolongs the internal design of the analyzer in such a way that all the components involved in this flow are involved. The quality of the flow obtained is one of the main reasons that cause the analyzer's resolution to be notably higher. So much so that, for the first time, it has been possible to carry out measurements of particle mobility in the sub-nanometer range.

Therefore, this invention involves various improvements both overall and specific that increase the resolution and measurement range of the analyser, as well as other properties such as response and analysis speed, simple maintenance, efficiency, analysis capability in the sub-nanometer range and sensitivity.

DESCRIPTION OF THE INVENTION

The analyzer in this invention represents an important development over the analyzers described above.

The basic configuration consists of a prismatic region with a rectangular base in which two opposing walls are made up of electrodes, the electrodes that define the electric field.

Two of the remaining opposing sides of the control volume defined by the prismatic region form the inlet and outlet of the flow, called cross flow because, except in special cases, it is perpendicular to the electric field. Depending on which opposing faces are chosen, these will be coplanar with or perpendicular to the electric field.

The entry of charged particles is carried out by electrostatic injection via a slit in one of the electrodes in such a way that the charged particle travels to the other electrode, driven by the electric field. The drag of the cross flow fluid establishes an impact band for particles of equal electrical mobility in the other electrode downstream.

The entry of charged particles is said to be carried out by electrostatic injection for two reasons: one because if it were carried out with the entry of a secondary flow, it could cause a jet or curtain that introduces turbulence and, secondly and more importantly, because at the speeds of the cross flow, the secondary flow appears as an obstacle that would generate shock waves, the appearance of large, non-stationary whirlpools, separation of the boundary layer and other unwanted phenomena. In order to achieve an injection of charged particles in these conditions, there must be no pressure differences on both sides of the slit. It is important to emphasise that there is no other exchange of fluid, except that of the charged particles or ions, between the analyzer and the inlet.

With respect to the region or area of impact, the normal practice in this invention is for it to be established on the opposing face to the injection, although this is not strictly necessary. In this area of impact there is at least one multi-track sensor and, optionally, when the target particle is to be extracted, there is an outlet slit. The analyzer in this invention may therefore use one or more slits combined with one or more multi-track sensors, which may be located below the outlet slit, above it or by simultaneously combining two, above and below it.

In order to carry out the adjustment of the analyzer, two variables may be used: the speed of the cross flow and the strength of the electric field. Depending on the mobility of the charged particle to be detected, both variables can be changed. By means of the design of the conduit through which the fluid flows, a field of speeds is determined which gives rise to a pressure close to that of the atmosphere in the analysis area so as to avoid leaks or entries of fluid to or from the exterior. Therefore, it will be the electric field that is adjusted by varying the potential difference between the electrodes.

The variation of one or other variable means that the particle that moves from the inlet slit travels to a point above or below the second outlet slit, when it exists. One possible adjustment consists of achieving that the particle enters the slot and that extraction can be carried out.

Part of this invention is the use of a multi-track charge sensor in such a way that, on a support, ceramic for example, a set of metallic micro-deposits is carried out along the lines, Each of these lines forms a conductor in such a way that they can be connected to a data output bus connected to a signal processor. The reading can be carried out in parallel.

It is also possible to establish a family of tracks distributed on lines that, instead of being equally spaced, are concentrated around a line, defining an area of higher resolution.

When the particle reaches this sensor, depending on the track where the impact is produced, it can be determined whether or not it is necessary to increase or reduce the electric field. In order for this sensor to be effective, the tracks must be parallel to both slits.

The use of two sensors operating simultaneously makes it possible to determine if it is necessary to increase or decrease the electrical potential according to whether the particles are arriving above or below the slot.

Likewise, simultaneous readings can be taken throughout the region defined by the area of the sensors regardless of whether a slit is used and of whether or not this slit performs the extraction.

Generally, differentiated extractions can be carried out with various slits each placed downstream of the other in such a way that each slit in turn has one or more multi-track sensors in order to be able to detect widely differing electrical mobilities. Therefore, the range of this apparatus is higher than that of others.

A more advanced configuration is that which makes use of integrated chips as a multi-track sensor. This chip would have charge collectors and would include the reading functions and even the pre-processing of the input data.

Emphasis has been made in this flat analyzer of the fact that it has slits and never perforations, which could give rise to possible transverse effects which cannot be considered two-dimensional.

Care has been taken to ensure that the slits do not reach the ends in order to avoid the wall and corner effects and that the presence of boundary layers in the flow cause three-dimensional disturbances in the ends of the slits, preventing the two-dimensional modelling and behaviour of the device. The special care that has been taken in the design of the contraction and of the chamfers with smooth evolution and adjusted using numerical simulations have resulted in a very uniform speed profile in the throat. Thus the three dimensional effects of the walls are very localised within 5% of the total width, allowing the width of the slot to be very close to the width of the throat or cross-section of the analysis area, preventing edge effects. At the same time the efficiency of the device is greatly increased, as the classification area is 80% or 90% of the travel area).

One of the possible modes of establishing higher resolution on the configuration of the analyzer consists of providing two or more analyzers in series. In this case, from the practical point of view, it is important to avoid potential differences between analyzers.

For this purpose, the use of multiple electrodes is proposed, at least two in the inlet, so that the analysis area has an electric field that is mainly oriented transversely to the cross flow, although the potential difference between the inlet and outlet electrodes is null. With this potential difference being null, two or more analyzers can be interconnected in series, so that each of them is adjusted in a range of narrower mobility and, as a result, achieving a much higher resolution. This technique also allows the interconnection of other equipment or accessories. The simplest case is when the inlet conduit is at the same potential as the outlet and at the same time in the inlet, this conduit is isolated from the feeder electrode. Since the inlet conduit is a conductor, as a final result, it could be considered that three electrodes are being used.

A second improvement consists of inserting one or more intermediary electrodes with slits that could simulate several analyzers operating in series, establishing intermediary discriminations that may reduce the degree of dispersion in the final reading in the sensor. This scheme reduces the effects of Brownian dispersion.

The other important factor in the increase in resolution is based on the careful design of a closed and pressurized aerodynamic wind tunnel for the cross flow. Although the details of this closed and pressurized aerodynamic tunnel will be described in the detailed description of the invention, it can be stated that this solution is responsible for the increase in the sensitivity and overall resolution of the device since it affects two variables that are responsible for resolution: the quality and uniformity of the cross flow (better signal to noise ratio) and the high Peclet number (increased resolution). The seal achieved together with the establishment of a closed area allows an increase in sensitivity. The pressurisation with pressures higher than atmospheric pressure is required in order to achieve the electrostatic injection and is only possible in its closed-circuit configuration. A set of solutions is established that provides a flow in the control volume defined by the analysis area with a Reynolds number that can reach $10^6$, preferably around $10^5$, with a degree of turbulence of less than 0.1%. The details of this design will be described in more detail in the example embodiment. Although the level of turbulence of 0.1% is indicated as the criterion for the undertaking of the invention because it is desired to reach a maximum level of resolution and sensitivity, by reducing the resolution criteria, this maximum level can be raised to 1%. Likewise, it can be stated that working in an almost sonic range provides two beneficial effects: raising the density, which also results in a higher Reynolds number and, above all, reducing the temperature, thus achieving a lower Brownian effect.

Another objective which has been achieved with the design of the cross flow circuit is that of occupying the minimum size so that this device can be used as a portable measurement device to detect target substances.

This invention may include an additional module in the outlet slit that increases the analyzer's resolution. This module can work either in the linear range or in the non-linear range of electrical mobility behaviour of the particles, although it is true that it is in the latter where the overall resolution of the analyzer is increased notably.

Electrical mobility has a weak dependence on the strength of the electric field and its behaviour may usually be described as being almost a constant. This behaviour is valid up to a certain value for the electric field where the electrical mobility starts to show its dependency on the electric field.

When two particles of a different nature show an electrical mobility value that is very similar in the linear range, the analyzer may confuse them and not be able to distinguish one from the other.

Once the two particles with very similar mobility have exited via the outlet slit, they enter this last module which consists of a conduit with electrodes on each side. The electrodes are polarized with an asymmetric wave and with a potential so that the strength of the electric field is sufficiently high that the behaviour enters the non-linear range. In this range, mobility is more clearly different, for which reason the trajectories will also be different.

When the polarization is alternate, a broken trajectory is obtained in which the displacement in one direction or another gives different displacement distances for each particle since the mobility in the non-linear range is clearly differentiated. Thus it is possible to discern between two particles which in the linear range show very similar behaviours in their typical curves. Nevertheless, it is possible to makes this last module work in the linear range.

DESCRIPTION OF THE DRAWINGS

This invention will be described in detail with reference to the accompanying drawings, in which.

DETAILED DESCRIPTION OF VARIOUS EMBODIMENTS

Figure 1:
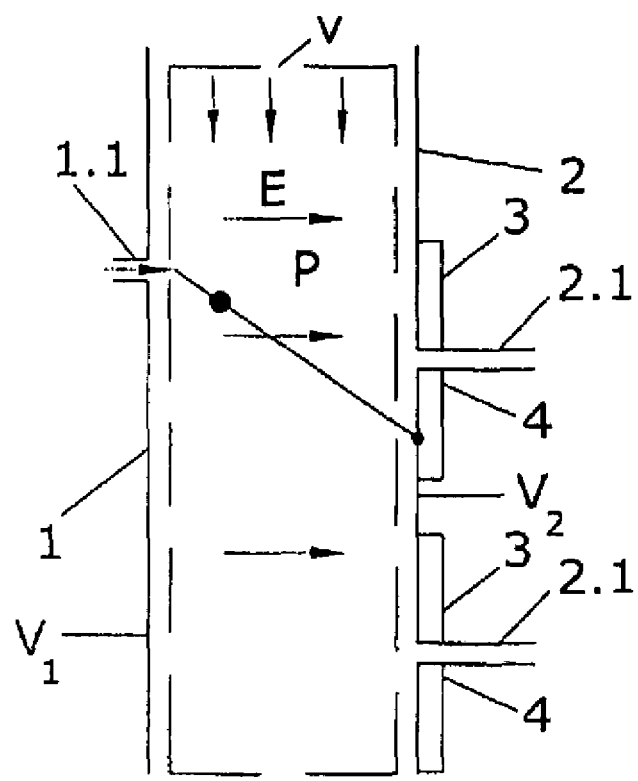
FIG. 1 is a representation of the analysis area of an analyzer according to this invention.

FIG. 1 is a scheme of the analyzer provided as an example for a detailed description of the invention, showing the analysis area determined by a control volume (V) called the analysis area. This analysis area is essentially prismatic on a rectangular base except for small changes, for example, at the edges, due to aerodynamic requirements.

The left of the figure shows the electrode (1) that occupies the vertical face fixed to a potential $V_1$ and to the right a second electrode (2) fixed to a potential $V_2$. The first electrode (1) shows an entrance slit (1.1) for the entry of charged particles that is essentially prolonged throughout the entire width measured in the direction perpendicular to the paper. In this example of embodiment, particles are extracted via a second slit (2.1) located in the second electrode. In these practical constructions, the slits (1.1, 2.1) can be said to be prolonged essentially throughout the width measured in the direction perpendicular to the paper, given that the ends do not reach the faces that delimit them, preventing disturbances due to the boundary layers both of these faces that delimit them and the vertices of the control volume (V). This precaution ensures that the problem is really two-dimensional. Nevertheless, it has already been stated that this locating of the ends of the slits (1.1, 2.1) is very small because the appearance of instabilities due to the effect of the corner has been minimized since, as described below, chamfers with a suitable evolution have been incorporated, adjusted using numerical simulations.

In this analysis area there is an electric field E (denoted E in bold since it is a vectorial magnitude), which extends from the left electrode to the right one.

According to the direction that will be used in the figures and especially in the first one, what has been called the cross flow throughout this description descends vertically, which is nothing more than a fluid crossing the analysis area (V) vertically at a high Reynolds number. In the tests carried out in order to construct the invention, Reynolds numbers higher than $10^5$ are being worked with. The flow is characterized by a stationary field of speeds v, which is very uniform and with a very low level of turbulence. The conditions that allow the maintenance of this flow in these conditions will be detailed further on.

The charged particle (P) leaves the slit (1.1) of the first electrode and is dragged by two forces, one to the right, due to the presence of the electric field E and the other, downwards, due to the drag of the fluid in which it is immersed.

Depending on the electrical mobility, the charged particle (P) will arrive above, in or below the second slit (2.1).

In this embodiment, two multi-track sensors (3, 4) have been used, one above and the other below the slit (2.1) so that it is possible to determine the point of incidence in order to correct the intensity of the electric field and, in turn, to adjust the place of impact or to make it exit through the second slit (2.1).

Emphasis has been placed on the need to achieve both a two-dimensional configuration and two-dimensional conditions for the electric fields and for the fluid dynamics in the analysis area (V).

The first condition is achieved using a support structure that allows the definition of flat parallel faces. The parallelism is achieved using calibrated shims for the plates that cover each face of the prism that delimits the analysis area (V).

If plates are used that are joined to beams at some of their edges, a serious problem arises, which is the difficulty of ensuring the sealing. If a gasket is built into the contact surface, this either does not define a closed-circuit or does not close all the possible routes that occur in the corners. Geometrically, sealing can only be achieved with a gasket in the form of a 3D cage. The manufacture of this type of gasket is complex and expensive.

As an alternative, by means a specific execution mode, it has been decided for the structure of the device to be a mechanized structure made with insulating material that uses the configuration in the form of a cage.

Figure 8:
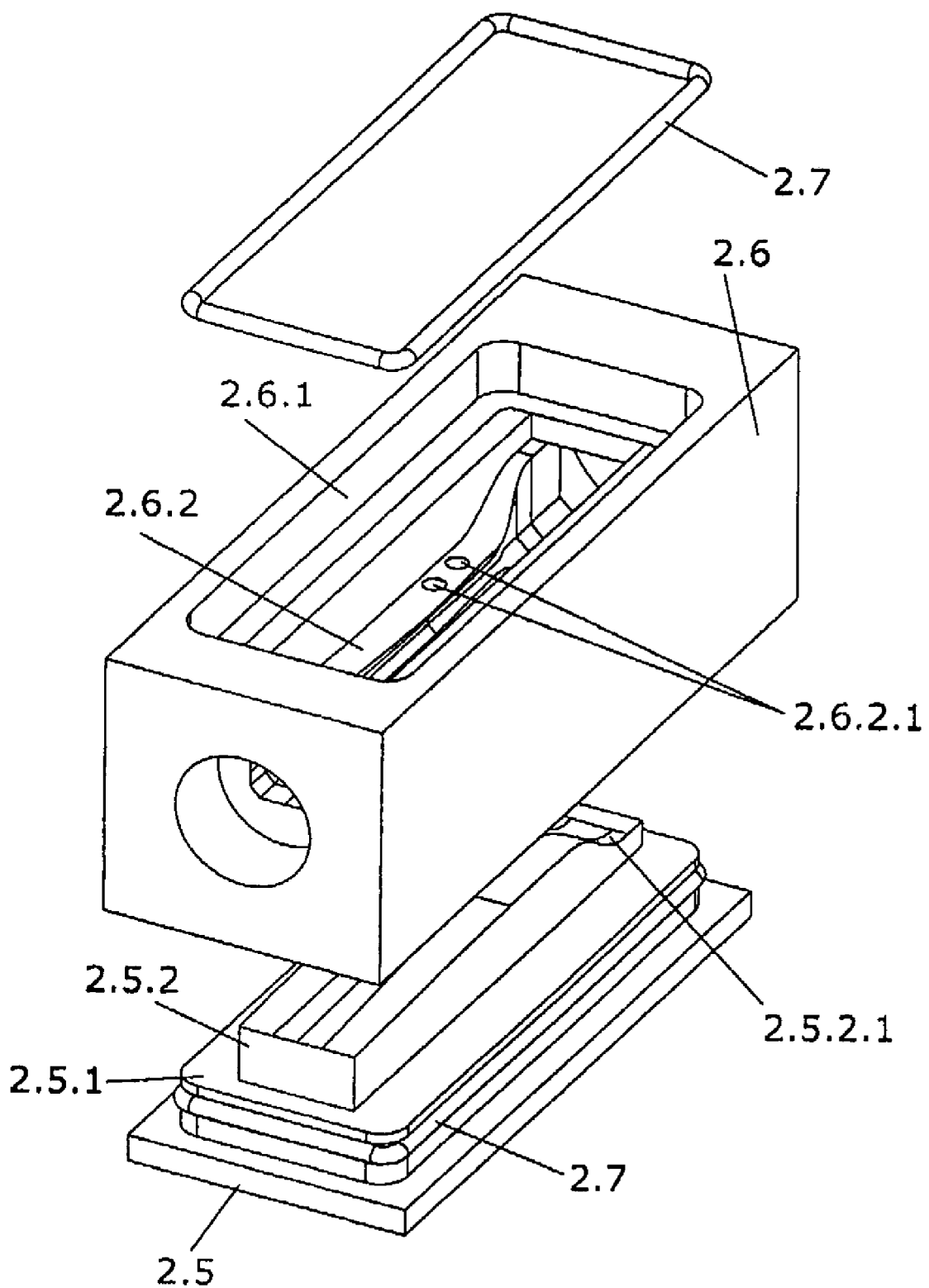
FIG. 8 shows an exploded view of the essential parts of the main body forming the analysis area.

As an example, FIG. 8 shows the structure of the main body (26) of the analysis area (V), a configuration that can be obtained, for example, by machining and by vacuum (26.1). The advantage of this structure, apart from its dimensional rigidity and stability, is the ease in achieving the parallel internal faces with the required degree of precision and, at the same time, a perfect seal because the configuration of each of the gaskets (27) may be closed.

The main body (26) is hollowed (26.1) in two of its larger opposing faces. These hollows (26.1) are closed by two lids with internal stepped ridges (25.1, 25.2). The outermost step (25.1) that has a housing with an O-ring (27) on its side face so that the adjustment does not depend on the tightening of the lid (25) against the main body (26). If this had been located on the front face, it would have been necessary to include a sufficiently high number of bolts in order to maintain even pressure on the gasket.

The upper lid (25) is not shown for clarity in showing the internal cavity of the main body (26), as well as the seatings.

The same figure shows how the stepped ridge (25.2) with a slightly curved surface (25.2.1) on the furthest shown end coincides with the curved surface (26.2) of the hollow (26.1) of the main body (26).

Nevertheless, the seating of this lid is carried out on the surface of some shims (26.2.1) which are found between the two lids (25). These shims (26.2.1) are nothing more than cylindrical bodies of very hard and rigid insulating material, machined to a high dimensional and geometrical precision to set the exact distance between their ends. Given that the lids (25) rest on these shims (26.2.1) without the need for adjustments, the required parallelism between the two lids (25) is achieved with precision, thus also achieving the parallelism between the walls that delimit the analysis area (V).

This mode of achieving the parallelism not only has implications in its embodiment, but also in its maintenance since the DMAs on the market with cylindrical configurations are difficult to disassemble for maintenance because of the serious difficulty of ensuring the coaxiality after assembly by the user and, therefore, the possibility of repeating the measurements.

Figure 2:
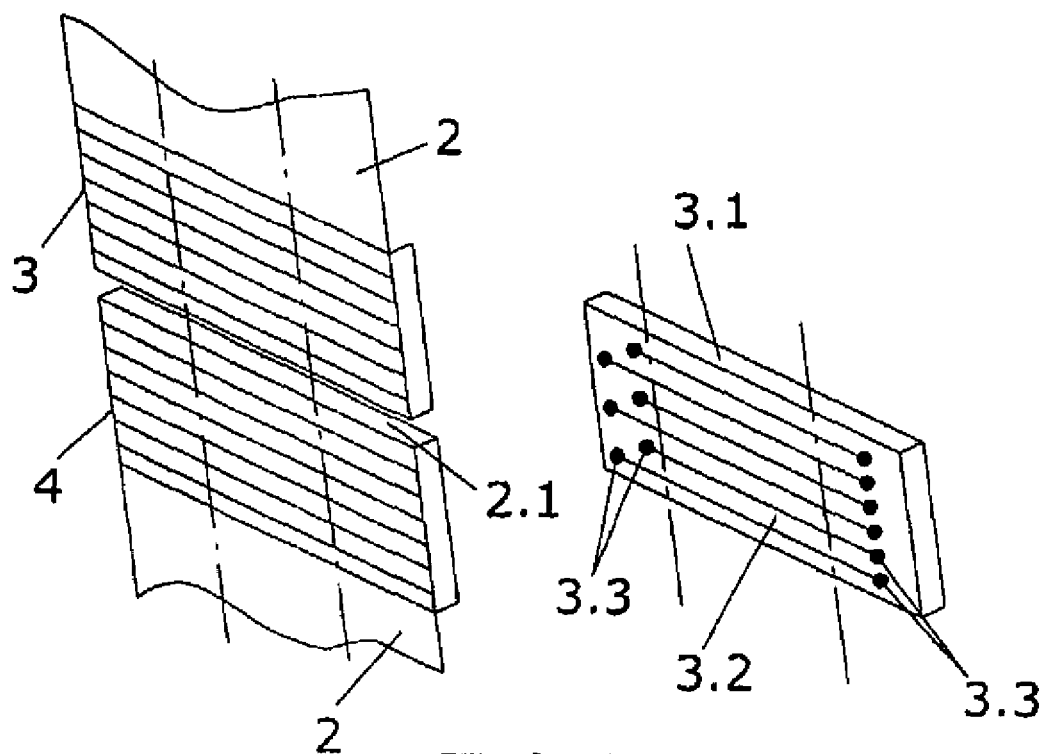
FIG. 2 is a schematic representation of the incidence surface with two multi-track sensors, showing a multi-track sensor in detail out of its final location.

FIG. 2 shows how this multi-track sensor has been built, this being considered an essential part of this invention. Any of the sensors (3, 4) used is made up of an insulating plate (3.1) onto which conducting metal micro tracks (3.2) are deposited. In this mode of constructing the invention, a deposition technique has been used because the relief generated by this deposition is almost void so that the flow is not disturbed, since no instabilities are generated that cause turbulence.

The laboratory tests that have been carried out used tracks with a height with respect to their deposition base of 0.1 μm. The width is of the order of 20 μm and the separation between micro tracks (3.2) is 2 μm to 5 μm.

Thickened contact points (3.3) are shown on the front face of the plate (3.1), which are also obtained by deposition.

This same representation also shows two dotted lines that represent the support places for the insulation plates that close the analysis area (V) laterally. Thus the contact points (3.3) are available on the exterior, facilitating contact for the reading of the signals, both because of their deposition and their larger contact area, for example using pressure test probes.

In the same representation and serving as an example, the thickened contact points (3.3) are shown aligned to the right and, to the left in alternating positions in order to allow a greater density of tracks (3.2).

This connection leads to a processor that can handle the signal, identifying whether an incident has occurred in a conducting track (3.2) of the sensor (3, 4). A reading made in this manner can be carried out in real time and simultaneously for each track (3.2) in the sensor. It is equally possible that this multi-track sensor be integrated in a chip, together with the reading and data pre-processing elements. The connection of this chip to an external processor would provide a higher level of data exchange since the processor would not need to evaluate the analogue signals obtained in a track signal.

One mode of creating this chip is using CMOS integration technology. The chip includes current pre-amplifiers, analogue to digital converters and digital multiplexing of the output signal. With a digital data output by vectors, with the reading values for each of the micro-tracks among others, a high parallel operating capacity is obtained, optimising the resolution of the individual measurement.

It is possible to build this invention with a single multi-track sensor (4), in such a way that the adjustment need only be made on one side.

This adjustment on one side means that if, for example, the sensor is in the lower part, it is necessary to start with a low potential in order to ensure that the particle impacts after passing through the slit (2). By raising the intensity of the electric field E, the impact point of the same type of particle (P) can be adjusted towards the slit (2). Since the sensor (4) is underneath, the presence of multiple lines gives rise to a progressive reading, which gives an idea of the degree of adjustment.

The presence of a multi-track sensor (3, 4) not only permits this initial adjustment to be carried out more quickly and reliably, but also allows multiple readings to be taken at the same time for different substances. The greater the number of lines per unit of transverse length of the tracks (3.2), the greater the spatial resolution of the sensor (3, 4) is. A special case is when all the readings are made by the sensor (3, 4) and there is no outlet slit (2.1) to extract the particles from.

Figure 3:
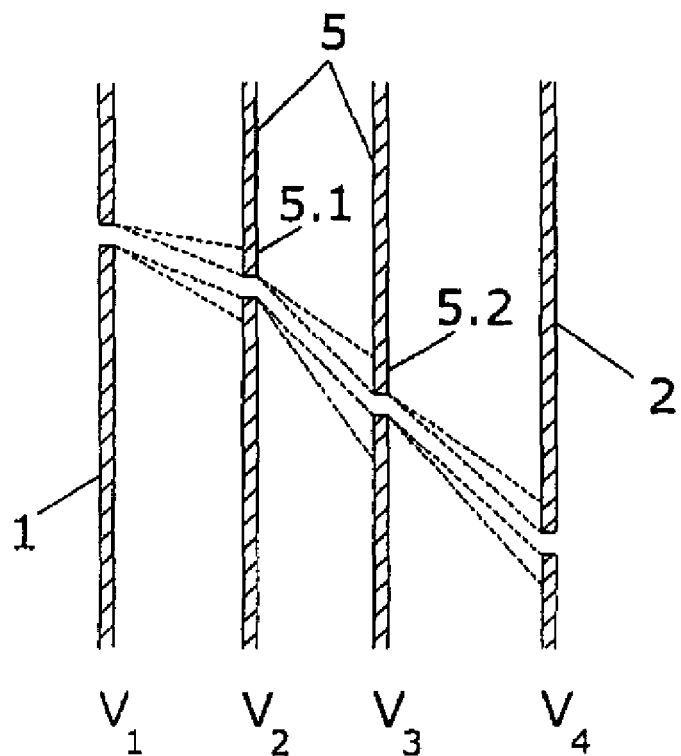
FIG. 3 is a schematic representation in which the use of more than one electrode in order for a reduction in the dispersion of the inlet data is shown.

One possible improvement to the analyzer consists of the use of more than one electrode (1, 2 and 5) as shown in FIG. 3. The presence of intermediate electrodes with suitable slots (5.1, 5.2) means that the particle that must enter the final slit (2.1) must first pass through various classification slits (5.1, 5.2). The fact of requiring passage through a larger number of slits in electrodes (5) with different potentials eliminates particles that increase the degree of dispersion in the final reading. The reduction of this degree of dispersion is affected not only by the presence of these intermediate electrodes (5) with slits (5.1, 5.2), but also involves the potentials and their configuration due to the fact that a broken trajectory may give way to a selection of the mobility defined over narrower ranges. This layout allows the effects of the dispersion caused by Brownian diffusion to be reduced.

It is also possible to use non-parallel electric fields E in such a way that electrostatic lenses can be used to force a certain degree of divergence that increases the distinction level for charged particles with similar electrical mobility. In these cases, the two-dimensional behaviour of the electric field E must be assured at all times. These distortions of the electric field may even cause the particles to exit through slits (2.1) located on the same side as the inlet slit (1.1).

Figure 4:
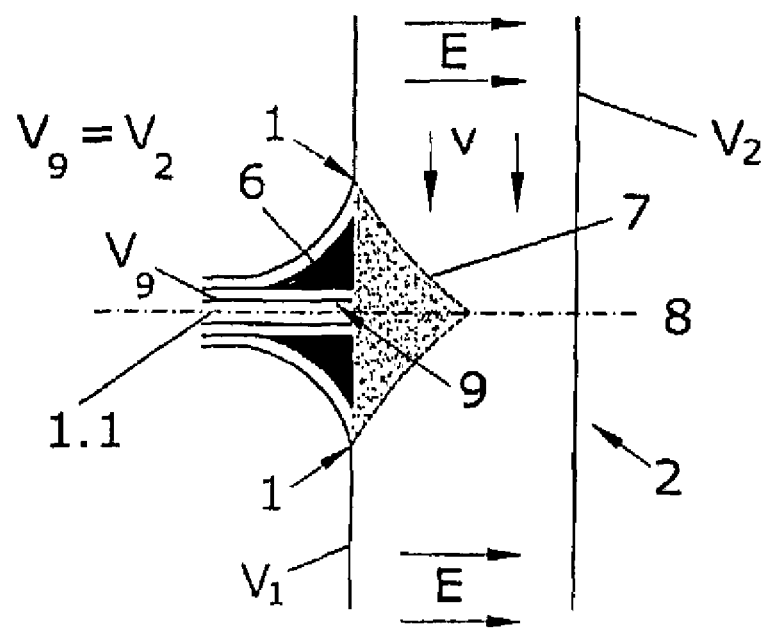
FIG. 4 shows a configuration of the analysis area with an electric field given by a combination of electrodes that have the same potential at the inlet as at the outlet.

FIG. 4 shows another mode of execution in which at least three electrodes (1, 2 and 9) are used. The vertical electrodes (1, 2), mainly coinciding those used in the basic scheme, except that the first one is curved near the slit (1.1) surrounding the third electrode (9) and spaced with an insulator (6). In this way, the following is verified:

$$V_2 = V_9 \text{ and } V_1 \neq V_9$$

Under these conditions, it is found that in the analysis area the electric field is parallel in the greater part of the control volume (V) and at the same time the potentials at the inlet and outlet are equal. Near the inlet slit (1.1) there is an area (7) with a symmetry plane (8) in which there is a distortion of the electric field E which must simply be taken into account. It is this condition that allows more than one analyzer such as that of the invention to be coupled sequentially, following a series layout that allows the resolution to be increased by various orders of magnitude. With two analyzers in series, the first would discriminate between particles with very different mobility and the second would allow the distinction between particles with very similar mobility. On the other hand, the coupling of two analyzers in series is normally used to calibrate one of the devices when the other has already been calibrated. Given that the two devices do not have equal potentials at the inlet and outlet, they have strong limitations in practice.

Figure 5:
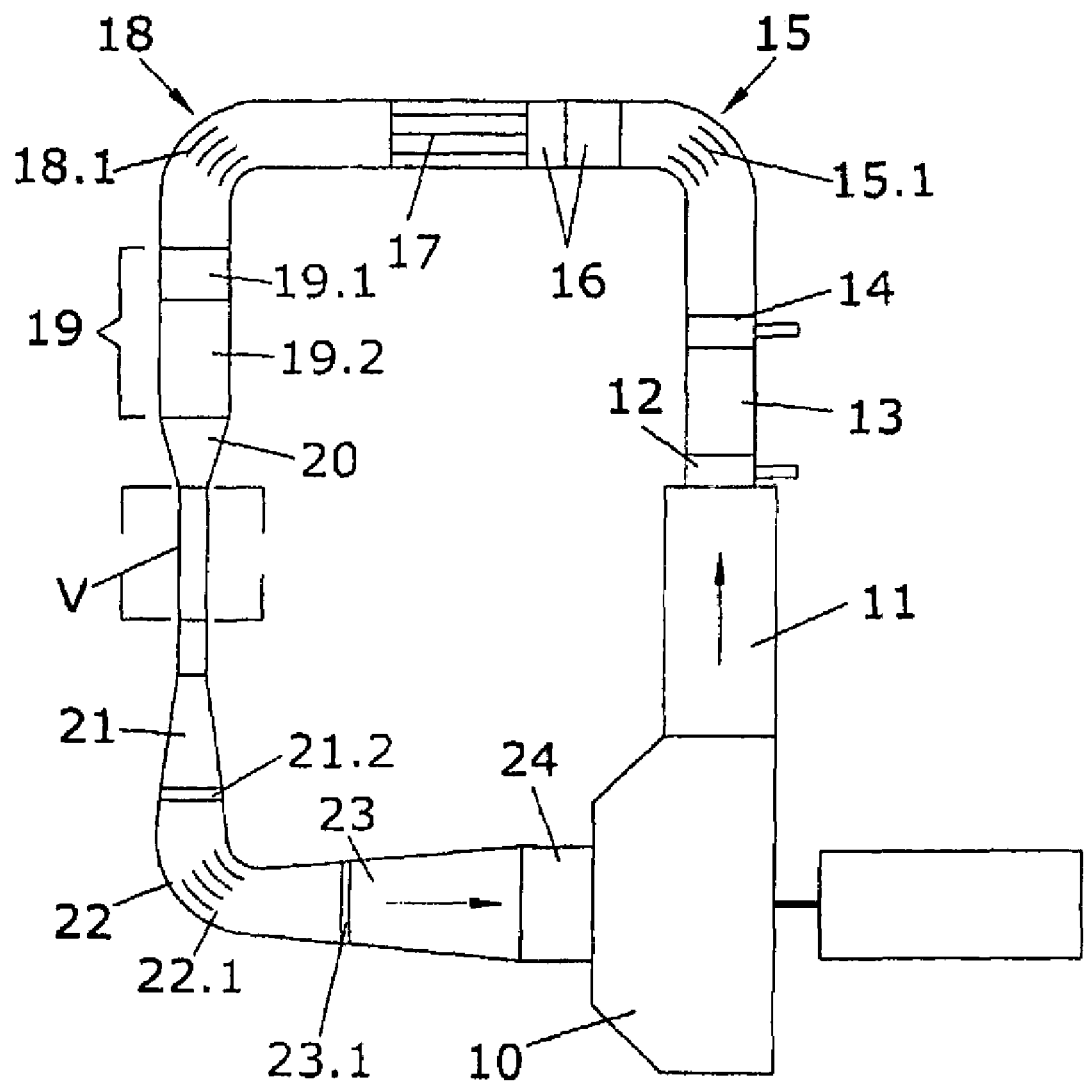
FIG. 5 shows a configuration scheme of the fluid recirculation circuit to form the closed invention.

FIG. 5 shows a general layout of the circuit for the cross flow. The description of this circuit starts with the compressor (10). The compressor (10) is the device responsible for maintaining the fluid in circulation. This fluid could be, for example, air or another gas that is free of impurities and particles that may affect the measurement in the analysis area. Cleanliness is an essential factor in the resolution of the DMA and not only because there are particles of dust or similar, but because the materials used in its construction must not release any type of substance since any release consists of particles that are similar to those to be detected. The compressor (10) is located in a corner of the circuit, replacing an elbow in order to avoid this type of section in which the fluid has to be forced to change direction, preventing the formation of vortices, movements of the boundary layer or instabilities that result in a non-laminar fluid. On leaving the compressor (10) it has a higher pressure and this decreases over the various stages of the circuit until the analysis area (V); it then starts to increase and recover part of the loss in pressure. The next stage is a flow meter (11) that allows the flow to be measured and, therefore, the speed (v) of the cross flow in the analysis area (V).

In this example of embodiment, a valve (13) has been placed between two bleeders (12, 14) so it is possible to feed the circuit from the possible flow extracted via the outlet slot and to replace the internal fluid periodically. This replacement is carried out by closing the intermediate valve (13) to inject the fluid via a bleeder (12) which drags that which already exists as it exits via the second bleeder (14).

Given that the main objective is to reach a high Reynolds number under flow conditions in which the level of turbulence is below 0.1%, a design is required that minimises, as far as possible, the generation of turbulence, the presence of secondary flows and large vortices and that at some point a separation or movement of the boundary layer is produced.

Given that the outlet of the compressor (10) has a circular cross-section and the analysis region area has a square cross-section, a transition area is needed between the two that does not generate excess vortices. Both the changes in the form of the cross-section and the restrictions in square cross-sections with changes according to different reduction factors give way to transverse components in the current which in turn could cause vortices which, if not controlled, develop into smaller vortices that could result in flows of greater turbulence downstream.

This control in the changes of cross-section has been carried out by adjusting the geometry on the basis of results from numerical simulations. As a result, a set of solutions has been adopted that prevent the appearance of secondary flows with areas of recirculation or the appearance of large-sized vortices.

Two elbows (15, 18) have been used to reach the analysis area. Given that the transition from a circular to a square cross-section has already occurred in the first straight section after the first elbow (15), these (15, 18) are of rectangular cross-section. The square cross-section makes the presence of coaxial vortices difficult.

Both the conduits and the rectangular cross-section elbows have chamfers that eliminate a large area of slow flow by converging the boundary layers of both faces.

In the elbows (15, 18) a variety of curved vanes (15.1, 18.1) have been included which guide the flow so that this follows the curve of the elbow, causing rotation along the curve and preventing centrifugal type instabilities.

Nevertheless, after passing through each set of vanes (15.1, 18.1), although the appearance of vortices of a size comparable to the transverse cross-section itself is prevented, the boundary layers of each vane (15.1, 18.1), as well as the compressor (10) itself and any solid obstacles, generate turbulent trails and it is because of this that it is necessary to homogenize the fluid and reduce turbulence.

In order to homogenize the flow, first a honeycomb turbulence manipulator, prismatic cells or a tube packaging (17) are used, which give way to a certain homogenization in such a way that the turbulence is more even than on entering.

To prevent the presence of particles that can introduce noise in the readings taken in the analysis area, the circuit has electrostatic precipitators (16) that allow for the withdrawal of charged or neutral particles that are ionized in the precipitator itself.

After passing through the second elbow (18), a second stage is used, consisting, for example, of a tube pack (19.1) or a panel of prismatic cells to smooth the flow, as well as grids (19.2) with a suitable porosity and grid, each operating on a different scale of the turbulence. Both sets (19.1 and 19.2) give way to a stage in of turbulence reduction or possible laminarization before the flow enters the analysis region.

The entrance to the analysis area (V) is carried out by means of a contraction (20), the cross-section of which progressively evolves and maintaining a moderated aspect ratio (in order) to avoid the different degrees of contraction produced in various directions from causing cross currents that (may) cause the movement of the boundary layer and to avoid separating the fluid in a two-dimensional model. This is one of the main lackings in cylindrical DMA's, as not only do they present sudden expansions due to the direct and even side feeding in cavities of a greater cross-section, but also the changes of cross-section vary according vertices of greater or lesser angle). The numerical simulations which have led to the configurations of the example have used surfaces that follow polynomical functions or partly polynomical functions in which the continuity of the curvature is demanded). This condition must be verified in order to prevent the introduction of possible points of disturbance in the boundary layer. The presence of cross flows or the non-two-dimensionality of the analysis area (V) would give way to different drag conditions depending on the point of observation in the inlet (1.1) and outlet (2.1) slits.

The pressure in the minimum area or throat region, which coincides with the analysis area (V), must be equal to that outside the slit so that there is no inlet or outlet flow. This implies pressurising the DMA, the opposite of what happens in known DMAs. The maximum pressure reached in the example analyzer is approximately 1.7 atm, for a Reynolds number of $10^5$ and a maximum Mach number of 0.98. If resolution is understood as the relative width of the peak of electrical mobility at half height, these values allow resolutions substantially below 1% to be obtained, thus notably improving the state of the art, in which no DMA has ever achieved a resolution of below 1%.

Once past the analysis area (V), a first diffuser (21) with a limited degree of divergence is used in order to prevent the movement of the boundary layer in the walls that may give way to recirculation flows. Expansion has not been carried out completely in this section, for which reason, after an elbow (22) with redirecting vanes (22.1), a second diffuser (23) is used, which also acts as the inlet to the compressor (10), thus closing the circuit.

This second diffuser (23) progressively adapts the configuration of the cross section until it matches the configuration of the inlet mouth of the compressor (10).

It is to be noted that, surprisingly, it has been found that the distance of the two diffusers arranged consecutively with an elbow between them form a length that is notably shorter than the length that would be required with a single diffuser. A plausible explanation is that the pressure jump that is established in the curved vanes (22) stabilises the flow, allowing a large degree of expansion in a smaller space. This stabilisation can be increased by including grids. In the example described, a first grid (21.2) is included in the first section (21) and a second grid (23.1) in the second section (23). These grids introduce a small, non-recoverable loss of pressure in exchange for the regeneration of the boundary layer, which is what allows the length of the diffuser to be the notably reduced.

Just before the compressor inlet (10), there is a heat exchanger (24) that reduces the temperature of the fluid before raising its pressure. The reduction in temperature causes an increase in density which allows the output of the compressor to be increased by up to 25%-30% in the tests carried out.

Likewise, the inclusion of radial redirectors in the compressor inlet (10) in order to reduce the transverse speed component makes the operation of the compressor (10) more efficient.

The result is a pressurized circuit with an average pressure greater than that of the atmosphere in such a way that, when operating, the maximum pressure is in the compressor outlet (10) and continues to fall to the inlet slit (1.1) which it is essentially at atmospheric pressure so as to avoid inlet or outlet flows, and later to recover greater pressure values in the diffusers, reaching those of the compressor inlet (10).

The described configuration of this circuit may not only be in the plane of the paper as in FIG. 5, but may also be arranged in a different plane, for example, perpendicular to the paper, so that circulation is carried out as if the analysis area (V) had been rotated 90 degrees on its axial axis.

Likewise, the solutions proposed for particular modes of configuring the analyzer in the analysis area (V) with the optional elements of the recirculation circuit are understood as being interchangeable.

After the particle (P) exits via the slit (2.1), additional devices can be included that increase the resolution. The aim is to discern between two particles with very similar electrical mobility that have been able to exit via the same slit (2.1). In this case, it is necessary to establish mechanisms in which the difference in mobility becomes more evident.

Figure 6:
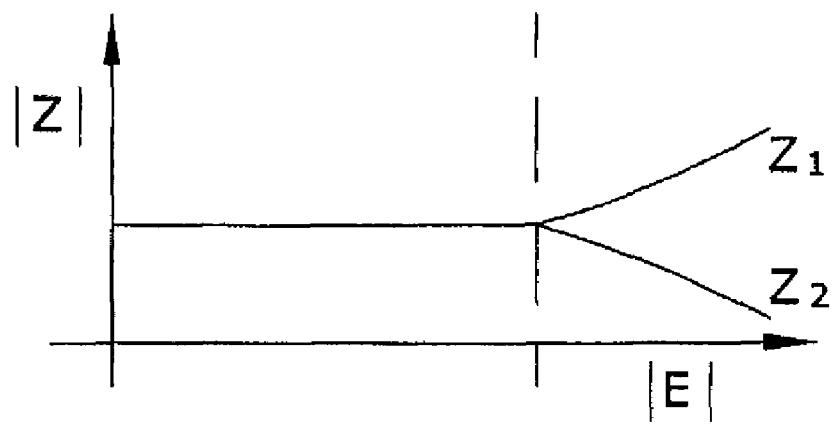
FIG. 6 is a graph that shows the electrical mobility with behaviour in the linear and non-linear area of two charged particles, so that its mobility in the linear range is indistinguishable.

This invention includes the optional use of a non-linear separation module in the outlet. FIG. 6 shows a graph of the typical mobility of a charged particle submitted to an electric field with a strength represented by the value of the module of the electric field |E|. Up to a certain value for the strength of the electric field, mobility is a function of linear behaviour and is approximately constant. Once having surpassed this critical value, behaviour is non-linear in such a way that two particles with very similar $Z_1$ and $Z_2$ mobility values in the linear range, may differ even in the value of their first derivative in their non-linear zone. The graph shows how a mobility value may be increasing and for another type of particle may be decreasing. This change in behaviour is used in the separation module. However, the module is equally useful when working in the linear range, except that the degree of divergence is not as pronounced as in the non-linear range.

Figure 7:
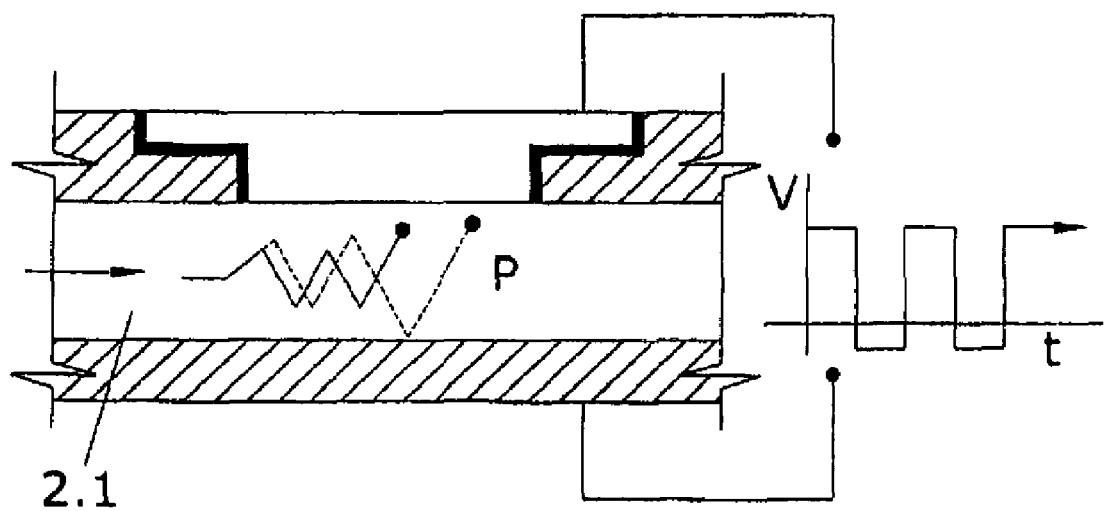
FIG. 7 shows a schematic cross-section of the conduit following the outlet slit with the selection module that uses the different electrical mobility in the non-linear range. This cross-section shows the upper electrode isolated from the conduit with a polarization indicated by the exciting function.

As shown in FIG. 7, the operational scheme of a selector module is known and consists of passing the charged particle through a channel between two electrodes. The potential difference between electrodes is defined as a wave, preferably asymmetrical and preferably with polarity inversion. Before a single electric field with enough intensity so as to be situated in the non-linear area of behaviour, two particles with characteristic curves such as those shown in FIG. 6 result give way to one of them being displaced with a transversal component to a greater degree than the other. Thus there will be particles that impact against the walls of the selector and those that are to be extracted that follow a broken exit trajectory thanks to the recovery of the position in the transverse direction due to the alternating form of the wave. The result is a broken trajectory in which two particles with similar mobility diverge to a greater degree. This divergence allows them to be discriminated, increasing the overall resolution of the analyzer.

The invention claimed is:

1. A wide-range and very high-resolution differential mobility analyzer (DMA), among the devices for discriminating chargeable particles that has an essentially prismatic analysis area with a rectangular cross-section in which an electric field is defined by the polarization of electrodes, likewise defining a cross flow wherein the cross flow is achieved by a closed, pressurized, aerodynamic wind tunnel with an average pressure greater than that of the atmosphere, free of sudden expansions and in laminar conditions or with a level of turbulence below 1% where the analysis area is essentially at atmospheric pressure and presents a configuration and two-dimensional conditions of the electric field E and of the cross flow where the injection of the charged particles is achieved by means of a slit essentially without the exchange of flow in the inlet, with the exception of the particles, in such a way that an area of impact is established that has at least one multi-track charge sensor.

2. A wide-range, very high-resolution differential mobility analyzer (DMA) as in claim 1, wherein the analyzer has one or more outlet slits, all arranged parallel to each other and perpendicular to the flow.

3. A wide-range, very high-resolution differential mobility analyzer (DMA) as in claim 1, wherein the analysis area has opposing electrodes, one on the charged particle injection face and the other on the outlet face, which generate an uniform electric field.

4. A wide-range, very high-resolution differential mobility analyzer (DMA) as in claim 3, wherein the electrodes cover opposing faces.

5. A wide-range, very high-resolution differential mobility analyzer (DMA) as in claim 3, wherein the electrode located on the charged particle injection face is prolonged parallel to the injection slit being insulated and facing a third electrode in such a way that the electric field is curved in injection and is maintained essentially parallel in the rest of the analysis area and where this third electrode is equal in potential to the outlet electrode in order to allow the chaining of analyzers.

6. A wide-range, very high-resolution differential mobility analyzer (DMA) as in claim 3, wherein the analysis area has additional electrodes, each with its slits with their own potentials establishing intermediate means of reducing dispersion.

7. A wide-range, very high-resolution differential mobility analyzer (DMA) as in claim 3, wherein the electric field has diverging areas in order to increase the differentiation of trajectories in particles of similar electrical mobility.

8. A wide-range, very high-resolution differential mobility analyzer (DMA) as in claim 7, wherein the outlet slit is on the same face as the injection.

9. A wide-range, very high-resolution differential mobility analyzer (DMA) as in claim 1, wherein the multi-track charge reading sensor is located downstream of each outlet slit.

10. A wide-range, very high-resolution differential mobility analyzer (DMA) as in claim 1, wherein some or all of the outlet slits have a second multi-track charge reading sensor located above the slit.

11. A wide-range, very high-resolution differential mobility analyzer (DMA) as in claim 1, wherein rectangular cross-section conduits are used except in the impulsion compressor so that there are transition areas in the section.

12. A wide-range, very high-resolution differential mobility analyzer (DMA) as in claim 1, wherein the compressor has an elbow in the circuit.

13. A wide-range, very high-resolution differential mobility analyzer (DMA) as in claim 1, wherein the elbows have multiple curved vanes and aligned in order to guide the interior flow.

14. A wide-range, very high-resolution differential mobility analyzer (DMA) as in claim 1, wherein the circuit has bleeders.

15. A wide-range, very high-resolution differential mobility analyzer (DMA) as in claim 1, wherein the circuit has valves for the cleaning and partial closing of the circuit.

16. A wide-range, very high-resolution differential mobility analyzer (DMA) as in claim 1, wherein the circuit has electrostatic precipitators for cleaning the charged particles.

17. A wide-range, very high-resolution differential mobility analyzer (DMA) as in claim 1, wherein between the two elbows located before the inlet to the analysis area a package of tubes, panel of prismatic or tubular cells are used in order to reduce the level of turbulence in the flow.

18. A wide-range, very high-resolution differential mobility analyzer (DMA) as in claim 1 wherein, between the analysis area and the elbow located before the inlet to the analysis area and this; a stage is used in order to condition and reduce the level of turbulence in the flow.

19. A wide-range, very high-resolution differential mobility analyzer (DMA) as in claim 17, wherein the stage for reducing the level of turbulence in the flow includes a package of tubes, panel of prismatic or tubular cells or a polygonal grid.

20. A wide-range, very high-resolution differential mobility analyzer (DMA) as in claim 18, wherein the flow lamination stage includes a package of tubes, panel of prismatic or tubular cells.

21. A wide-range, very high-resolution differential mobility analyzer (DMA) as in claim 1, wherein there is a diffuser in two sections, one section after the analysis area and another section before the compressor inlet compressor separated by an elbow with redirecting vanes.

22. A wide-range, very high-resolution differential mobility analyzer (DMA) as in claim 21, wherein there are grids between the diffuser in two sections in order to stabilise the flow.

23. A wide-range, very high-resolution differential mobility analyzer (DMA) as in claim 1, wherein the conduits are chamfered in order to prevent the appearance of areas of recirculation close to the corners.

24. A wide-range, very high-resolution differential mobility analyzer (DMA) as in claim 1 wherein after the exit slit there is a linear or non-linear separation module consisting of two electrodes fed by a polarization using an asymmetric wave of alternating polarity to establish diverging broken trajectories for distinguishing between particles of very similar electrical mobility.

25. A wide-range, very high-resolution differential mobility analyzer (DMA) as in claim 1 wherein, before the compressor inlet, there is a heat exchanger in order to reduce the temperature.

26. A wide-range, very high-resolution differential mobility analyzer (DMA) as in claim 1 wherein the sensor is a chip containing the current pre-amplifiers, analogue/digital converters and digital multiplexing of the output signal.

27. A wide-range, very high-resolution differential mobility analyzer (DMA) as in claim 1 wherein the main body that forms the analysis areas has hollows in the larger opposing faces covered by lids separated by shims that are held by the perfect parallelisms between the lids.

* * * * *